(12) United States Patent
Rhee et al.

(10) Patent No.: US 6,274,195 B1
(45) Date of Patent: Aug. 14, 2001

(54) ORGANOMETALLIC COMPLEX PROCESS FOR THE PREPARATION THEREOF AND METAL ORGANIC CHEMICAL VAPOR DEPOSITION USING SAME

(75) Inventors: Shi-Woo Rhee, Pohang-si; Jae-Young Shim, Kyungsangbuk-do; Jung-Hyun Lee, Seongnam-si; Dae-Hwan Kim, Pohang-si, all of (KR)

(73) Assignee: Postech Foundation (KR)

( * ) Notice: Subject to any disclaimer, the term of this patent is extended or adjusted under 35 U.S.C. 154(b) by 0 days.

(21) Appl. No.: 09/560,448

(22) Filed: Apr. 28, 2000

(30) Foreign Application Priority Data

Apr. 30, 1999 (KR) .................................................. 99-15557
Jan. 25, 2000 (KR) .................................................... 00-3371

(51) Int. Cl.⁷ ................................ C23C 16/06; C07F 7/00
(52) U.S. Cl. .................... 427/255.31; 556/56; 427/248.1
(58) Field of Search ........................... 556/56; 427/248.1, 427/255.31

(56) References Cited

U.S. PATENT DOCUMENTS 4,568,703 * 2/1986 Ashida .................................. 521/124

OTHER PUBLICATIONS

Bharara et al., Chemical Abstracts, vol. 83, No. 2, p. 769, abstract No. 21225f, Jul. 1975.*
Bharara et al., Synth. React. Inorg. Met.–Org. Chem., vol. 7, No. 6, pp. 537–546, 1977.*

* cited by examiner

*Primary Examiner*—Porfirio Nazario-Gonzalez
(74) *Attorney, Agent, or Firm*—Anderson Kill & Olick, PC

(57) ABSTRACT

An organometallic complex of formula(I) having a low evaporation temperature can be used as a precursor for the MOCVD of a metal compound thin film on semiconductor devices

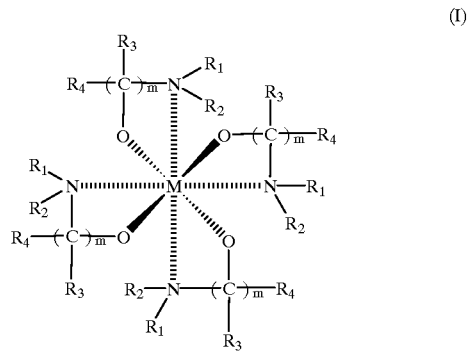

wherein, M is Ti or Zr;

$R_1$, $R_2$, $R_3$ and $R_4$ are each independently H or $C_{1-4}$ alkyl; and m is an integer ranging from 2 to 5.

3 Claims, 7 Drawing Sheets

ORGANOMETALLIC COMPLEX PROCESS FOR THE PREPARATION THEREOF AND METAL ORGANIC CHEMICAL VAPOR DEPOSITION USING SAME

FIELD OF THE INVENTION

The present invention relates to an organometallic complex useful as a precursor for a thin metal compound layer fabricated in semiconductor devices, a process for the preparation thereof and metal organic chemical vapor deposition using same.

BACKGROUND OF THE INVENTION

Semi-conductor devices have recently become more highly integrated and smaller in size than ever before, which generated needs to develop sophisticated materials and processes for forming thin films in the fabrication of semiconductor devices. In response to such needs, there have been developed, for example, barium strontium titanate (BST) used in a capacitor for dynamic random access memory(DRAM), and ferroelectric materials such as lead zirconate titanate(PZT), strontium bismuth titanate(SBT), bismuth lanthanum titanate(BLT) used in ferroelectric random access memory(FRAM) and yttrium stabilized zirconia (YSZ) and metal oxides such as $TiO_2$ and $ZrO_2$. Thin films of such materials are prepared by using such techniques as radio frequency magnetron sputtering, ion beam sputtering, reactive co-evaporation, metal organic decomposition (MOD), liquid source misted chemical decomposition (LSMCD), laser ablation and metal organic chemical vapor deposition(MOCVD).

Among these methods, MOCVD is carried out by vaporizing one or more organometallic precursor compounds, transporting, using a carrier gas, the vaporized precursor(s) to the surface of a heated solid substrate and forming a thin film on the surface of the substrate through a chemical reaction. The MOCVD method is advantageous in that: it can be carried out at a relatively low temperature; the constitution and deposition rate of the thin film can be readily controlled by changing the amounts of the source materials and the carrier gas; and the final thin film has good uniformity and excellent conformal step coverage without causing any damage on the surface of the substrate. Therefore, MOCVD is widely used in manufacturing semiconductor devices such as DRAM and FRAM.

Generally, a precursor for CVD is required to have such properties as a high vapor pressure, high purity, high deposition rate, easy handling, nontoxicity, low cost and a suitable deposition temperature. However, conventional organometallic compounds for CVD such as metal alkyls, metal alkoxides and β-diketonates have many drawbacks. For example, metal alkyls having relatively high vapor pressures such as $Pb(C_2H_5)_4$ are very toxic (see Reference of Organometallic Dictionary). Metal alkoxides are sensitive to moisture, which relatively expensive metal β-diketonates have low vapor pressures and are solids at room temperature, posing handling difficulties in CVD process (see Anthony C. Jones et al., *Journal of the European Ceramic Society*, 19(1999), 1431–1434).

Besides the above problems, $Ti(O^iPr)_4$(titanium tetraisopropoxide) is unstable at room temperature and a thin layer obtained from $Ti(O^iPr)_2(tmhd)_2$(tmhd= tetramethylheptanedionate) has a fluctuating amount of Ti depending on the substrate temperature(see Jung-Hyun Lee et al., *Electrochemical and Solid-State Letters*, 2(10) (1999), 507–509).

SUMMARY OF THE INVENTION

Accordingly, it is an object of the present invention to provide a nontoxic organometallic complex which has a good thermal stability; is not sensitive to moisture; stays in the liquid form at room temperature; and can be conveniently used in a low temperature MOCVD for the production of a contaminant-free metal oxide film having a good conformal step-coverage In accordance with on aspect of the present invention, there is provided an organometallic complex of formula(I):

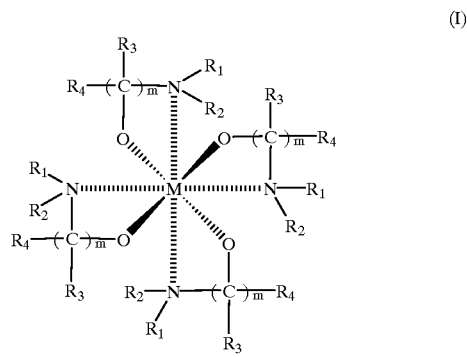

(I)

where, M is Ti or Zr;
$R_1, R_2, R_3$ and $R_4$ are each independently H or a $C_{1-4}$ alkyl group; and
m is an integer ranging from 2 to 5.

In accordance with another aspect of the present invention, there is provided a process for preparing an organometallic complex of formula(I) which comprises the steps of: mixing a metal compound of formula(II) or (III) with an amine compound of formula(IV) in an organic solvent in a molar ratio ranging from 1:4 to 1:5 and refluxing the mixture:

$$M(NR_2)_4 \qquad (II)$$

$$M(OR')_4 \qquad (III)$$

$$HO\text{—}(CR_3R_4)_m\text{—}NR_1R_2 \qquad (IV)$$

wherein, R and R' are each independently, a $C_{1-4}$ alkyl;
$R_1, R_2, R_3$ and $R_4$ are each independently H or a $C_{1-4}$ alkyl; and
m is an integer ranging from 2 to 5.

In accordance with still another aspect of the present invention, there is provided a process for depositing a metal oxide compound film on a substrate which comprises the steps of vaporizing the organometallic complex of formula (I) of claim 1, optionally together with one or more organometallic precursors, at a temperature ranging from 20 to 300° C. and bringing the resulting vapor into contact with the substrate heated to a temperature ranging from 300 to 600° C.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
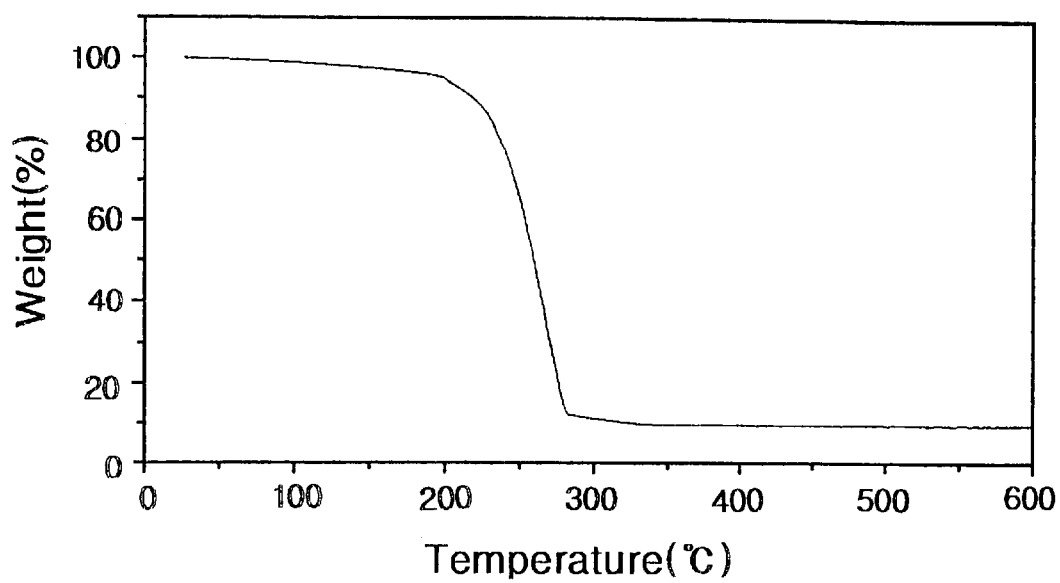
FIG. 1: the TGA scan of $Ti(dmap)_4$ obtained in Example 1 of the present invention.

Among the compounds of formula(I), preferred are titanium tetra(dimethylaminopropoxide) (Ti(dmap)$_4$), zirconium tetra(dimethylaminoethoxide) (Zr(dmae)$_4$) and titanium tetra(dimethylaminoethoxide) (Ti(dmae)$_4$), which are represented by formulae (V) to (VII), respectively:

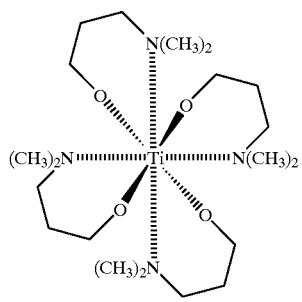

(V)

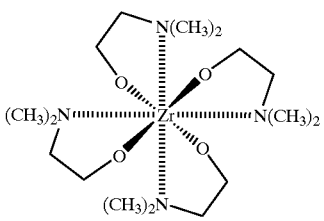

(VI)

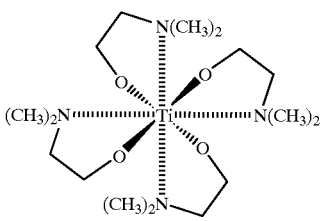

(VII)

The compound of formula(I) of the present invention can be prepared by reacting a titanium or zirconium compound with an amine compound of formula(IV).

The titanium or zirconium compound which can be used in the present invention is the compound of formula (II) or (III) and preferred are titanium tetra(diethylamine), zirconium tetra(diethylamine), titanium tetraalkoxide, zirconium tetraalkoxide. The representative amine compound which can be used in the present invention include N,N-dimethylpropanolamine, N,N-dimethylethanolmine and the like.

The solvent which may be used in the preparation of the compound of formula(I) is a conventional organic solvent such as hexane, toluene and pentane. The metal compound of formula(II) or (III) and the amine compound of formula (IV) may be employed in a ratio ranging from 1:4 to 1:5. Refluxing the resulting mixture for 15 to 20 hours gives the desired compound of formula(I) in a yield of 90% or more.

The organometallic compound of formula (I) of the present invention is a liquid at room temperature and highly volatile at a low temperature, and thus, it can be used as a precursor for CVD for fabricating a metal-containing thin film on a semi-conductor device. For example, the present invention can be used as a precursor by employing a conventional MOCVD method to obtain a thin layer of a metal oxide compound, e.g., a metal oxide such as TiO$_2$, ZrO$_2$(see Anthony C. Jones et al., *Chemical Vapor Deposition*, 4(2) (1998), 46–49), and YSZ(Yttrium stabilized zirconia) (see C. Dubourdieu et al., *Thin Solid Films*, 339 (1999), 165–173) or a ferroelectric material such as BST(barium strontium titanate)(see Jung-Hyun Lee et al., *Electrochemical and Solid-State Letters*, 2(10) (1999), 507–509), PZT(lead zirconate titanate)(see Anthony C. Jones et al., *Journal of the European Ceramic Society*, 19 (1999), 1431–1434), SBT(strontium bismuth titanate) (see C. Isobe et al., *Integrated Ferroelectrics*, 14 (1999), 95–103), BLT (bismuth lanthanum titanate).

In practicing the present invention, the CVD process for the formation of a metal compound thin film using the inventive organometallic precursor may be carried out by vaporizing the inventive precursor at 20 to 300° C. and transporting the resulting vapor with a carrier gas to the surface of a substrate heated to a temperature ranging from 300 to 600° C., more preferably, 400 to 550° C., under a reduced pressure, e.g., 0.1 to 10 torr.

The precursor may be vaporized by conventional bubbling delivery or liquid delivery. The bubbling delivery may be carried out by passing a carrier gas through a liquid precursor held in a container and the liquid delivery, by injecting a measured amount of a liquid precursor into an evaporator. In case of a liquid delivery process, the precursor may be diluted with an organic solvent such as tetrahydrofuran(THF), n-butylacetate and the like. The substrate which can be used in the present invention includes a conventional silicon substrate and a silicon substrate coated with Pt, Ir, IrO$_2$, Ru, RuO$_2$, SrRuO$_3$ or others. The thickness of the metal compound film may be conveniently controlled by adjusting the deposition time.

The following Examples and Test Examples are given for the purpose of illustration only, and are not intended to limit the scope of the invention.

EXAMPLE 1

Preparation of Ti(dmap)$_4$ (1)

Ti(O$^i$Pr)$_4$(titanium tetraisopropoxide)(18.45 g, 65 mmol) was added to 150 ml of dry hexane and N,N-dimethylpropanolamine(DMPA)(30.76 ml, 260 mmol) was added slowly thereto. The mixture was refluxed for 20 hours, and then, cooled. The solvent was removed under a reduced pressure to obtain an orange liquid, which was distilled at 150° C. to give Ti(dmap)$_4$ as a dark brown liquid.(Yield >90%).

A TGA scan of Ti(dmap)$_4$ thus obtained is shown in FIG. 1.

$^1$H NMR (CDCl$_3$ 300 MHz): δ 4.61(t, CH$_2$, 8H), 2.43(t, CH$_2$, 8H), 2.20(s, CH$_3$, 24H), 2.90(t, CH$_2$, 8H).

EXAMPLE 2

Preparation of Ti(dmap)$_4$ (2)

Ti(Net$_2$)$_4$(titanium tetradiethylamine)(21.87 g, 65 mmol) was added to 150 ml of dry hexane and N,N-dimethylpropanolamine(DMPA)(30.76 ml, 260 mmol) was added slowly thereto. The mixture was refluxed for 20 hours, and then, cooled. The solvent was removed under a reduced pressure to obtain Ti(dmap)$_4$ as a dark brown liquid.(Yield >90%).

$^1$H NMR (CDCl$_3$ 300 MHz): δ 4.61(t, CH$_2$, 8H), 2.43(t, CH$_2$, 8H), 2.20(s, CH$_3$, 24H), 2.90(t, CH$_2$, 8H).

EXAMPLE 3

Preparation of Ti(dmae)$_4$

Ti(O$^i$Pr)$_4$(10 g, 35 mmol) was added to 150 ml of dry hexane and N,N-dimethylethanolamine(DMEA)(12.5 g, 140 mmol) was added slowly thereto. The mixture was refluxed for 20 hours, and then, cooled. The solvent was removed under a reduced pressure to obtain Ti(dmae)$_4$ as a dark brown liquid. (Yield >90%).

$^1$H NMR (CDCl$_3$ 300 MHz): δ 4.34(t, CH2, 8H), 2.55(t, CH2, 8H), 2.28 (s, CH3, 24H)

EXAMPLE 4

Preparation of Zr(dmae)$_4$

Ti(NEt$_2$)$_4$(zirconium tetra(diethylamine))(24.68 g, 65 mmol) was added to 150 ml of dry toluene and N,N-dimethylethanolamine(DMEA)(26 ml, 260 mmol) was added slowly thereto. The mixture was refluxed for 20 hours, and then, cooled. The solvent was removed under a reduced pressure to obtain Zr(dmae)$_4$ as a colorless liquid.(Yield >90%).

Figure 2:
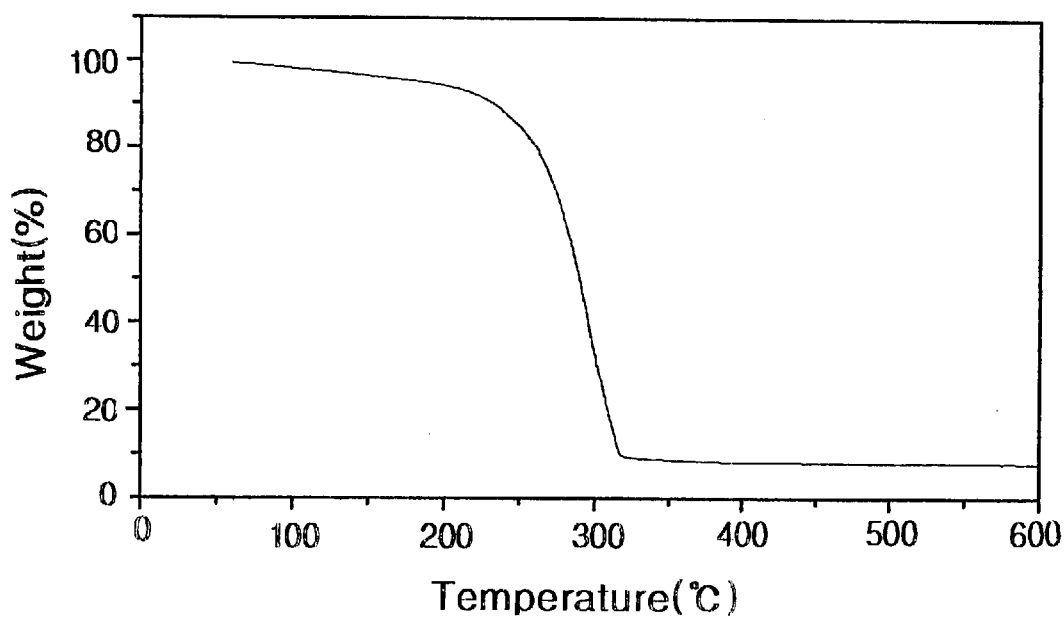
FIG. 2: the TGA scan of $Zr(dmae)_4$ obtained in Example 4 of the present invention.

A TGA scan of Zr(dmae)$_4$ thus obtained is shown in FIG. 2.

$^1$H NMR (CDCl$_3$ 300 MHz): δ 4.09(t, CH$_2$, 8H), 2.48(t, CH$_2$, 8H), 2.16(s, CH$_3$, 24H)

TEST EXAMPLE 1

Thermal Stability

Figure 3A:
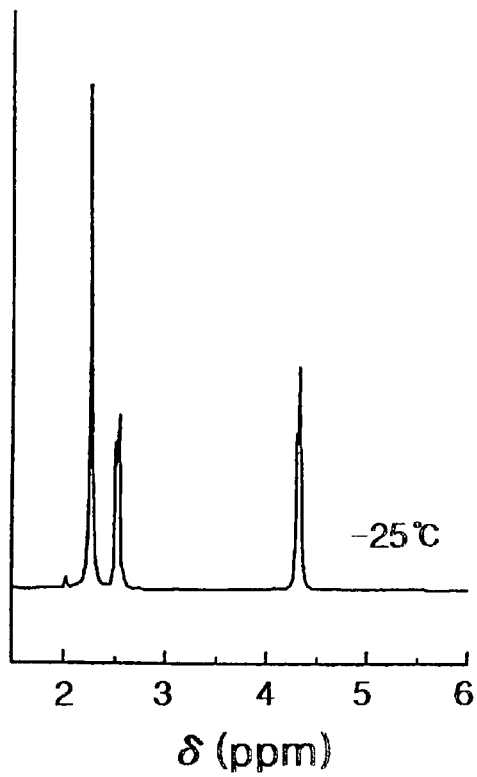
FIG. 3A and 3B: NMR spectra of Ti(dmae)$_4$ obtained in Example 3 of the present invention taken at −25° C. and 60° C., respectively.
Figure 3B:
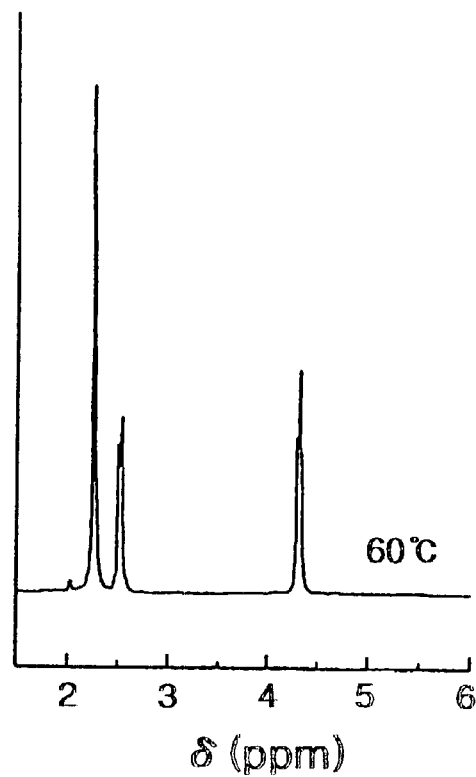

FIGS. 3A and 3B show NMR spectra of Ti(dmae)$_4$ taken at −25° C. and 60° C., respectively. As can be seen from FIGS. 3A and 3B, the NMR spectrum of Ti(dmae)$_4$ at −25° C. is identical to that taken at 60° C. This suggests that the organometallic complex of the present invention is thermally stable at 60° C.

TEST EXAMPLE 2

Mass Analysis

Figure 4:
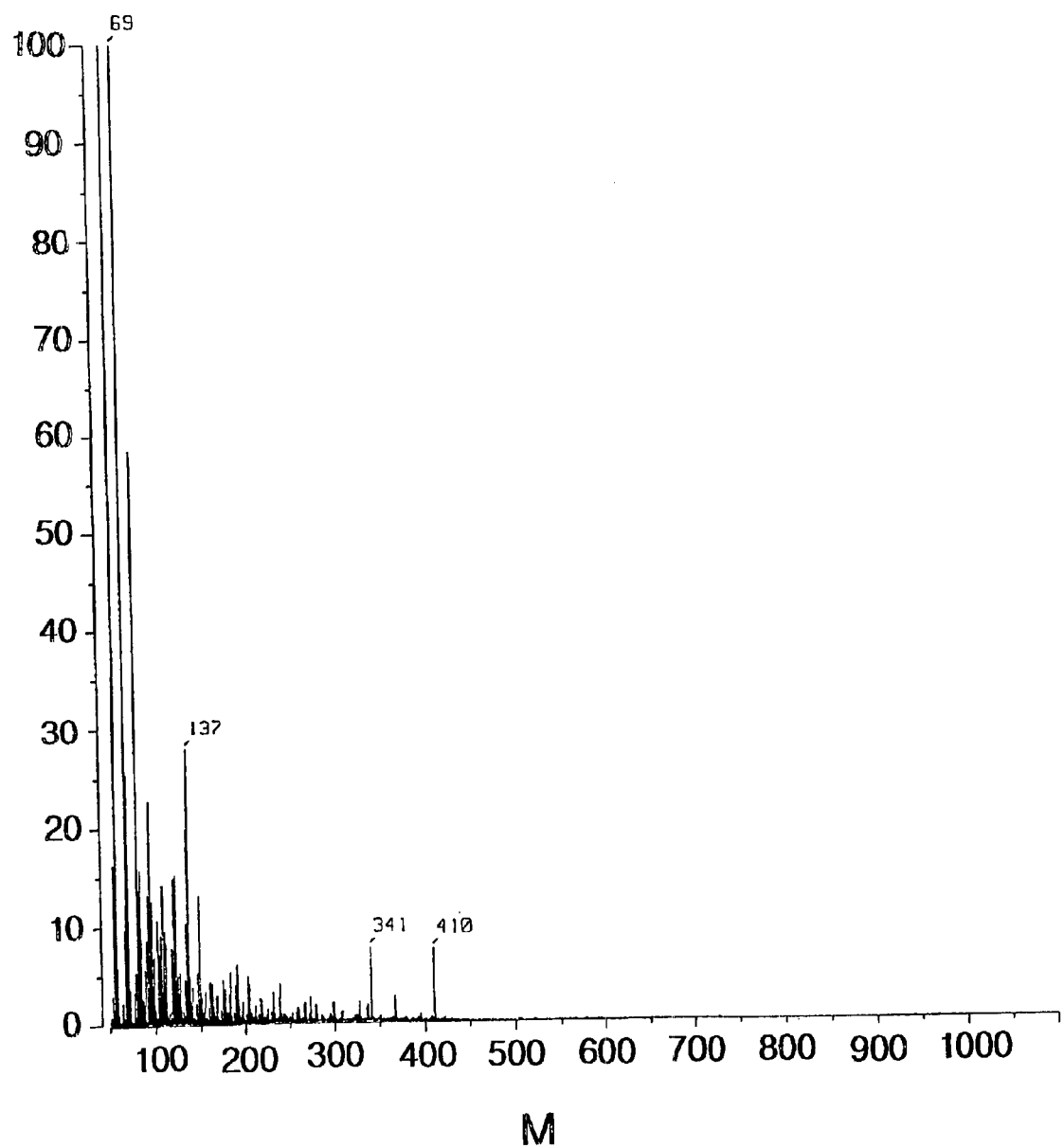
FIG. 4: the mass spectrum of Ti(dmap)$_4$ obtained in Example 1 of the present invention.
Figure 5:
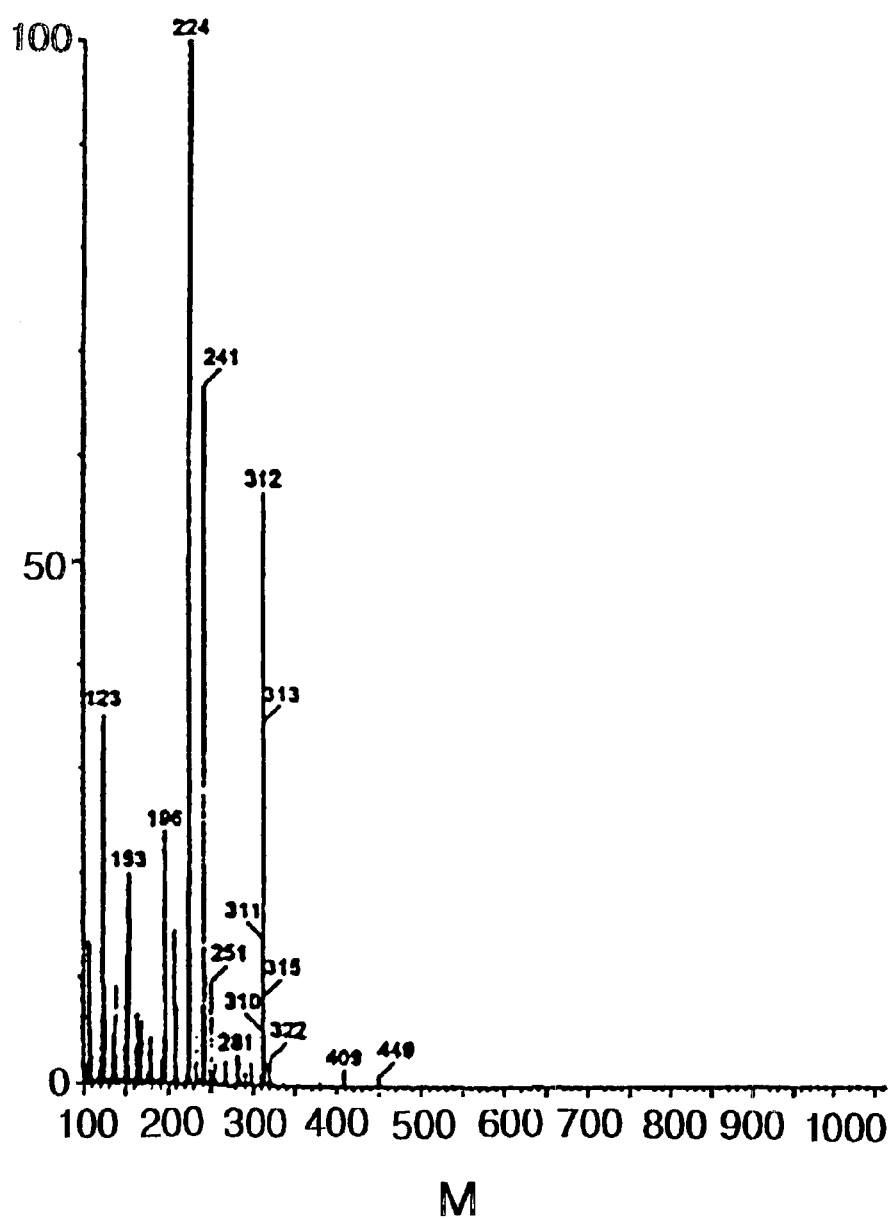
FIG. 5: the mass spectrum of Ti(dmae)$_4$ obtained in Example 3 of the present invention.
Figure 6:
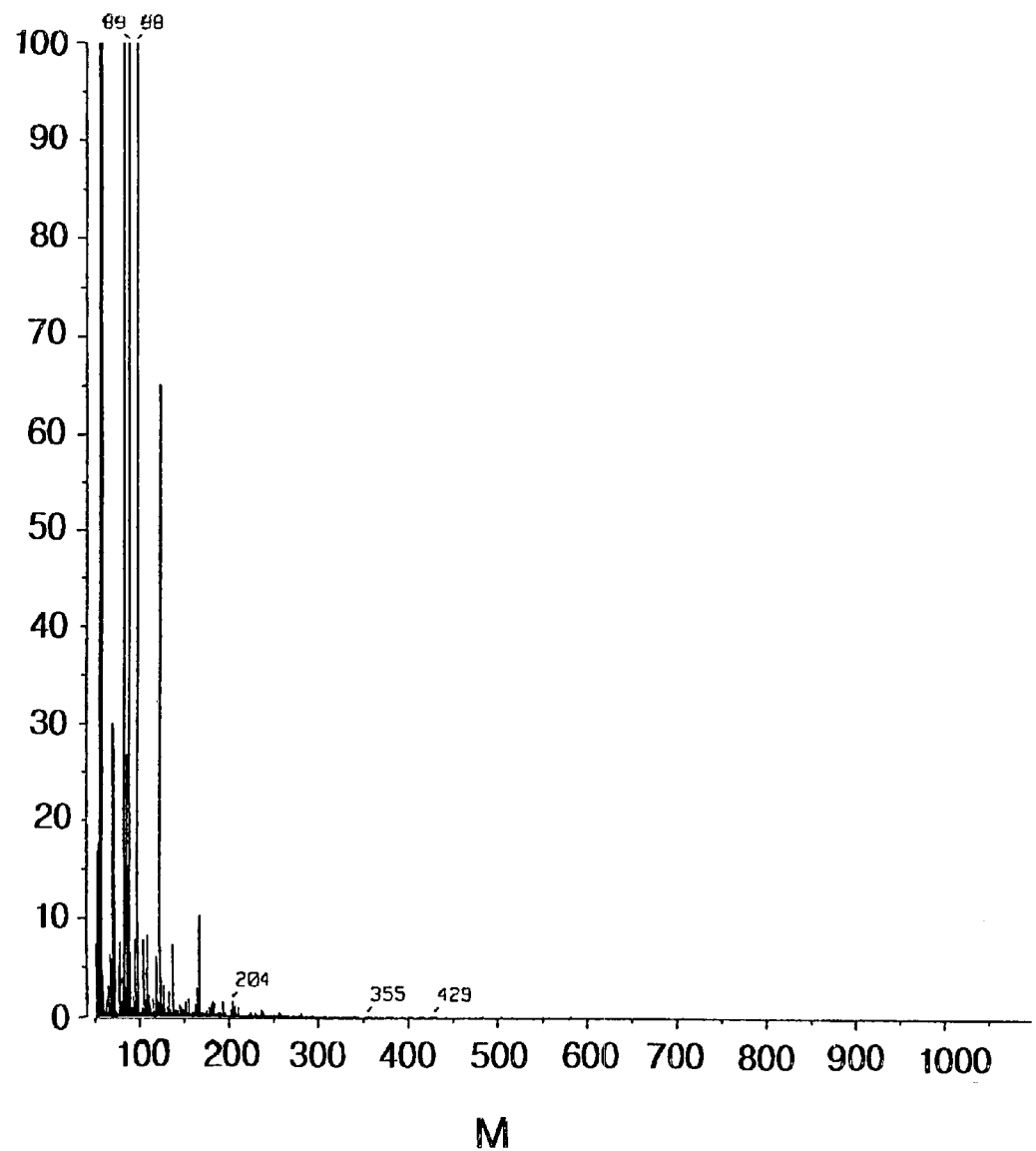
FIG. 6: the mass spectrum of Zr(dmae)$_4$ obtained in Example 4 of the present invention.

FIGS. 4 to 6 represent mass spectra of Ti(dmap)$_4$, Ti(dmae)$_4$ and Zr(dmae)$_4$, respectively. As can be seen from FIGS. 4 to 6, no peaks were observed after the peak corresponding to the molecular weight of each compound, i.e., 457, 401 and 444 for Ti(dmap)$_4$, Ti(dmae)$_4$ and Zr(dmae)$_4$, respectively. This suggests that each of the inventive compounds exists in a single molecule form and does not form aggregates.

TEST EXAMPLE 3

Evaporation Temperature

Generally, an organic precursor used in CVD of a thin film on a semiconductor device is required to vaporize at a temperature in the range of 200 to 260° C. in case of employing liquid delivery. As can be seen from FIGS. 1 and 2, Ti(dmap)$_4$ and Zr(dmae)$_4$, inventive organometalic complexes of the present invention, evaporate at 200 to 260° C. and thus can be effectively used as a CVD precursor.

Figure 7:
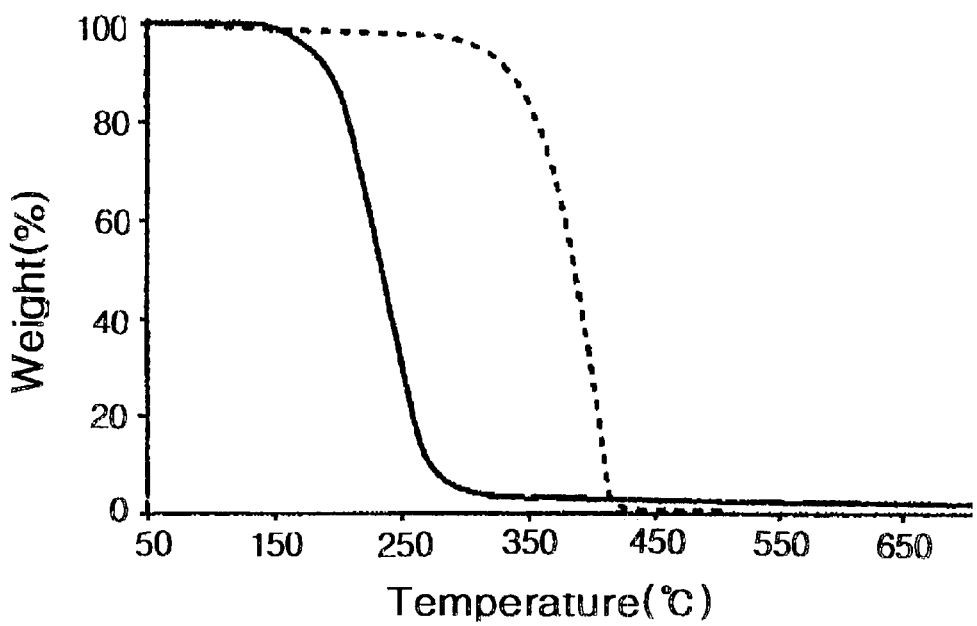
FIG. 7: TGA scans of conventional organometallic complexes.

In contrast, as shown in FIG. 7 by a broken line, the vaporization of conventional precursor, Zr(TMDH)$_4$ (zirconium tetrakis-2,2,6,6-tetramethyl-3,5-heptandione) of formula(VIII), begins after 350° C. which is too high for CVD. Further, although another conventional precursor, Zr(TMDH)(O$^i$Pr)$_3$ (zirconium 2,2,6,6-tetramethyl-3,5-heptandione) of formula(IX), begins to vaporize at 250° C. (FIG. 7, solid line), it is a solid at room temperature, posing a handling difficulty. Accordingly, the inventive compounds are more suitably used in MOCVD than the conventional precursors.

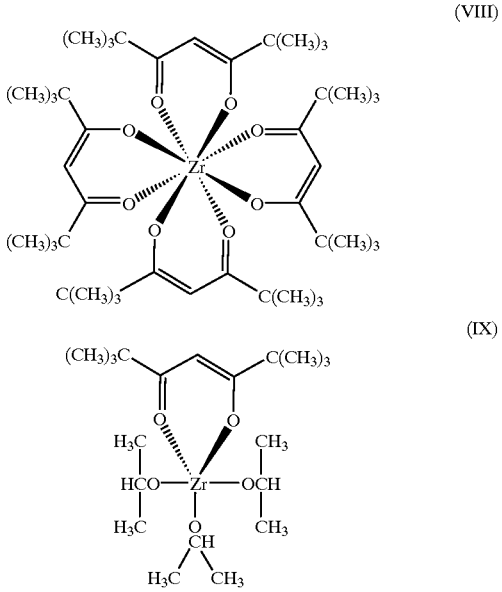

TEST EXAMPLE 4

Thin Layer Deposition

TiO$_2$ and ZrO$_2$ thin films were formed on a substrate by MOCVD employing Ti(dmae)$_4$ and Zr(dmae)$_4$ obtained in Examples 3 and 4, respectively, as the precursors under the conditions of evaporation temperature(vaporizer): 250° C.; the carrier gas flow rate: Ar/O$_2$:300/300(sccm); deposition time: 20 min.; and the concentration of the precursor: 0.2M(in THF). The growth rate of the deposition layer was measured as the substrate temperature was changed as in FIGS. 8(Ti(dmae)$_4$) and 9(Zr(dmae)$_4$).

Figure 8:
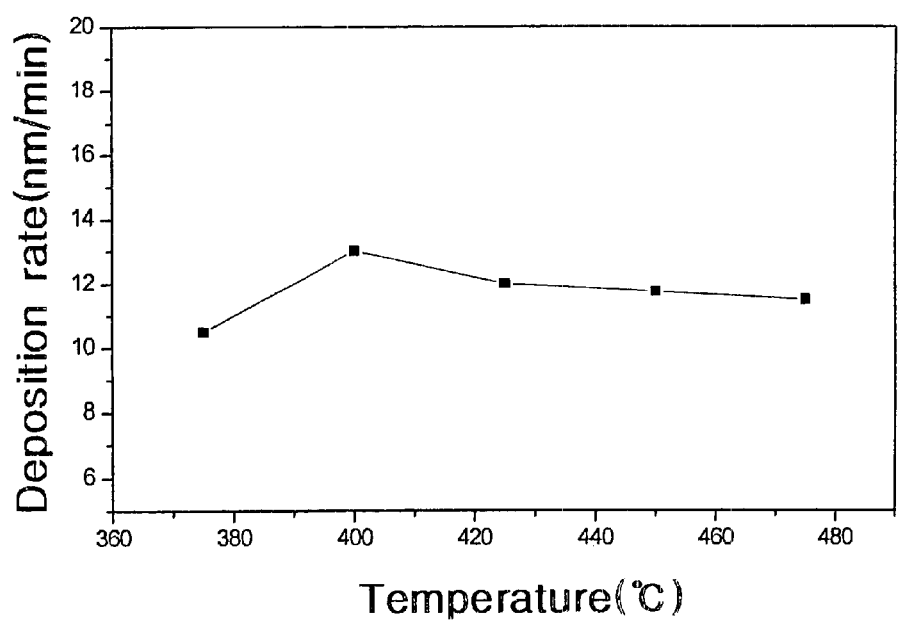
FIG. 8: the change in the TiO$_2$ deposition rate with the substrate temperature in a CVD process using Ti(dmae)$_4$ obtained in Example 3 of the present invention.
Figure 9:
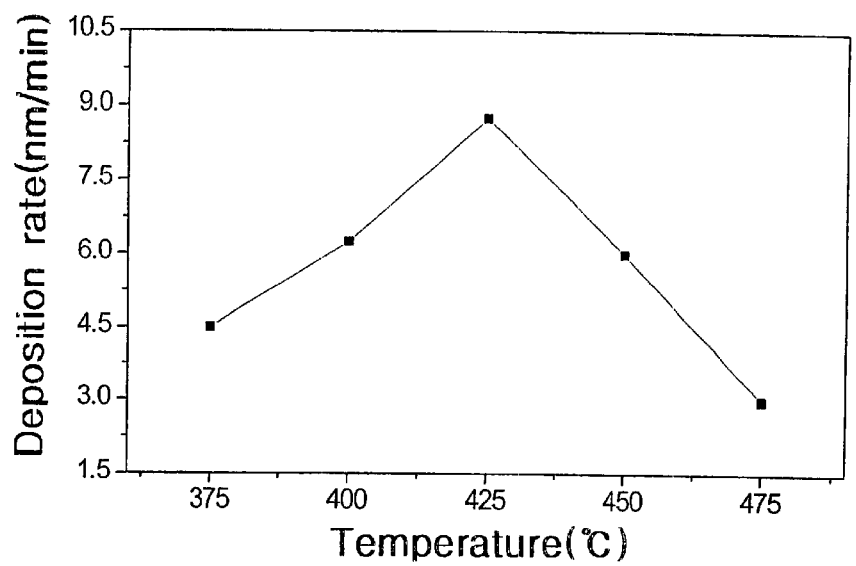
FIG. 9: the dependence of the ZrO$_2$ deposition rate on the substrate temperature in a CVD process using Zr(dmae)$_4$ obtained in Example 4 of the present invention.

As can be seen from FIG. 8, when $TiO_2$ was deposited by employing $Ti(dmae)_4$, the deposition rate peaked at a substrate temperature of about 400° C., and then, tapered off gradually toward 500° C. Therefore, $Ti(dmae)_4$ can be effectively used as a CVD precursor to from a $TiO_2$ thin film. Similarly, when $ZrO_2$ was deposited by employing $Zr(dmae)_4$, the deposition rate peaked at a substrate temperature of about 425° C. (see FIG. 9). Therefore, $Zr(dmae)_4$ can also be effectively used as a CVD precursor to from a $ZrO_2$ thin film.

TEST EXAMPLE 5

Deposition of BST Thin Film

A BST thin film was formed on a $Pt/TaO_x/SiO_2/Si$ substrate by MOCVD employing $Ti(dmae)_4$ obtained in Example 3 as a precursor. As the starting materials for Ba and Sr,. $Ba(thd)_2L$ and $Sr(thd)_2L$(thd=2,2,6,6-tetramethyl-3,5-haptanedionate, L=PMDT) were used and the molar ratios of Ba:Sr:Ti were controlled at 1:1:2. The deposition was conducted under the conditions of evaporation temperature (vaporizer): 270° C.; Ar 200 sccm, $O_2$ 400 sccm, $N_2O$ 400 sccm; and the substrate temperature: 400 to 500° C.

Figure 10:
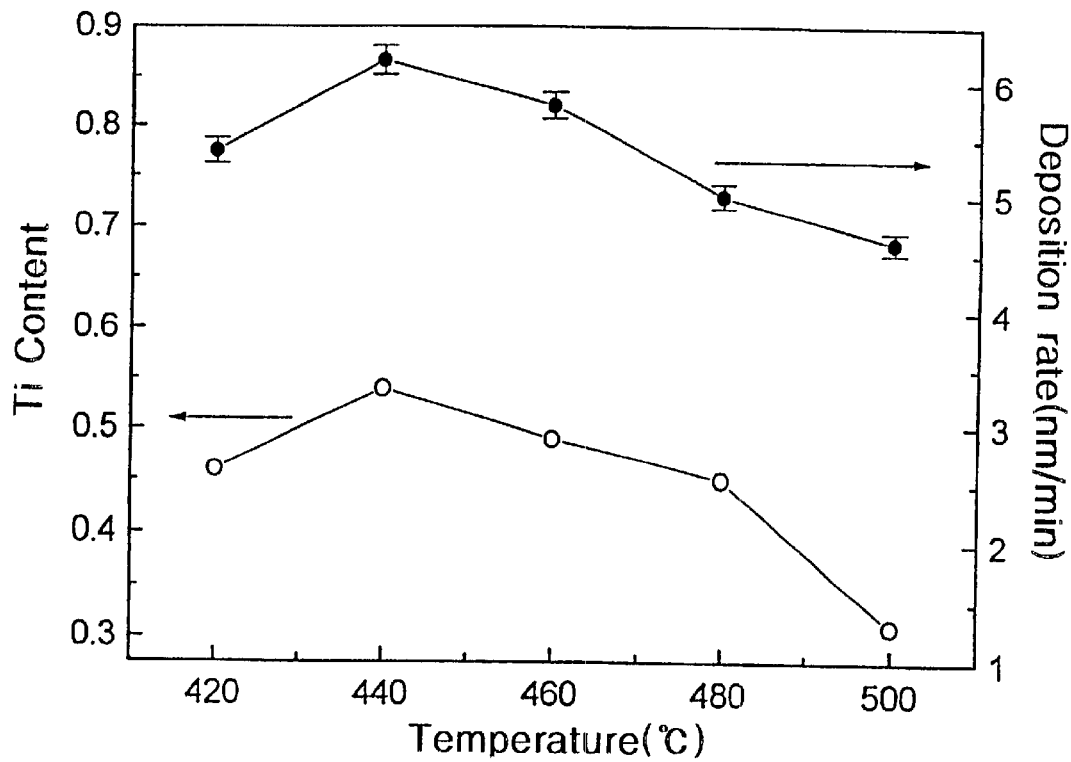
FIG. 10: the changes in the BST deposition rate and Ti content with the substrate temperature in a CVD process using Ti(dmae)$_4$ obtained in Example 3 of the present invention.

FIG. 10 shows the changes in the growth rate of the BST film(right) and the Ti fraction based on the total metal(left) with the substrate temperature. As can be seen from FIG. 10, the growth rate is high at 420–480° C. and the Ti content remains more or less constant in that temperature range.

Therefore, the inventive compound of the present invention can be used for CVD of various ferroelectric composite thin films on a semi-conductor device.

While the embodiments of the subject invention have been described and illustrated, it is obvious that various changes and modifications can be made therein without departing from the spirit of the present invention which should be limited only by the scope of the appended claims.

What is claimed is:

1. A process for depositing a metal oxide compound film on a substrate which comprises the steps of vaporizing the organometallic complex of formula (I) optionally together with one or more organometallic precursors, at a temperature ranging from 20 to 300° C. and bringing the resulting vapor into contact with the substrate heated to a temperature ranging from 300 to 600° C.:

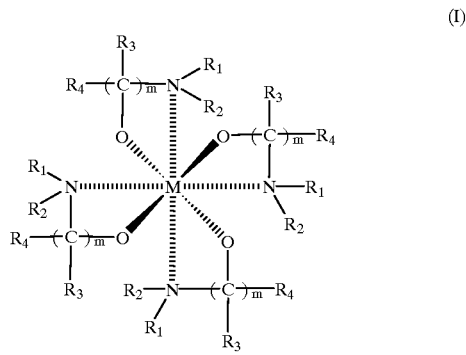

(I)

wherein,
M is Ti or Zr;
$R_1$, $R_2$, $R_3$ and $R_4$ are each independently H or $C_{1-4}$ alkyl; and
m is an integer ranging from 2 to 5.

2. The method of claim 1 wherein the metal oxide compound is zirconium oxide or titanium oxide.

3. The method of claim 1 wherein the metal oxide compound is selected from the group consisting of barium strontium titanate(BST), lead zirconate titanate(PZT), strontium bismuth titanate(SBT), bismuth lanthanum titanate (BLT) and yttrium stabilized zirconia(YSZ).

* * * * *